United States Patent

Wantier et al.

Patent Number: 5,478,564
Date of Patent: Dec. 26, 1995

[54] PREPARATION OF MICROPARTICLES FOR CONTROLLED RELEASE OF WATER-SOLUBLE SUBSTANCES

[75] Inventors: Henri Wantier, Dour; Fabienne Mathieu, Nivelles; Marc Baudrihaye, Waterloo; Dominique Delacroix, Kraainem, all of Belgium

[73] Assignee: Teva Pharmaceutical Industries, Ltd., Petah Tiqva, Israel

[21] Appl. No.: 77,501

[22] Filed: Jun. 17, 1993

Related U.S. Application Data

[63] Continuation of Ser. No. 810,403, filed as PCT/EP91/00307, Feb. 18, 1991, abandoned.

[30] Foreign Application Priority Data

Feb. 22, 1990 [FR] France .................. 90 02189

[51] Int. Cl.$^6$ .............. A61K 9/58; A61K 9/50; B01J 13/04
[52] U.S. Cl. .......... 424/426; 424/1.25; 424/1.33; 424/462; 424/486; 424/497; 427/213.36; 428/402.21; 514/963
[58] Field of Search ............ 264/4.6; 427/213.36; 428/402.21; 424/462, 486, 497, 426

[56] References Cited

U.S. PATENT DOCUMENTS

| | | | |
|---|---|---|---|
| 3,887,538 | 6/1975 | Shields et al. | 530/326 |
| 4,384,975 | 5/1983 | Fong | 427/213.36 |
| 4,492,720 | 1/1985 | Mosier | 264/4.6 X |
| 4,637,905 | 1/1987 | Gardner | 264/4.3 |
| 4,711,782 | 12/1987 | Okada et al. | 264/4.6 X |
| 4,863,970 | 9/1989 | Patel et al. | 514/784 |
| 5,100,669 | 3/1992 | Hyon et al. | 427/213.36 X |
| 5,232,707 | 8/1993 | Lokensgard | 424/497 X |

FOREIGN PATENT DOCUMENTS

| | | |
|---|---|---|
| 0102265 | 11/1984 | European Pat. Off. . |
| 2237545 | 2/1974 | Germany . |

*Primary Examiner*—Richard D. Lovering
*Attorney, Agent, or Firm*—Foley & Lardner

[57] ABSTRACT

The subject of the present invention is a process for preparing microparticles of the microsphere type of a water-soluble substance and a biocompatible and biodegradable polymer controlling the kinetics of release of the said substance consisting of a matrix of the said polymer within which the said water-soluble substance is regularly dispersed, characterized in that a) the said polymer is dissolved in a first volatile organic solvent immiscible with water, b) the said water-soluble substance is dissolved in a second solvent which is miscible with the said first solvent, is a solvent for the polymer, and miscible with water, c) the solution of the said substance and the solution of the said polymer are mixed, d) an organic phase of the polymer and of the said substance is obtained which is then emulsified in an immiscible dispersant medium consisting of an aqueous phase containing an emulsifying agent, e) the two solvents are then removed from the microspheres being formed with stirring, the first solvent being removed by evaporation, the second solvent and part of the first solvent which is miscible therewith being removed by passage towards the aqueous phase by a mechanism of phase separation, f) after removal of the solvents, the microspheres formed are recovered, optionally after washing in water and sieving.

9 Claims, No Drawings

PREPARATION OF MICROPARTICLES FOR CONTROLLED RELEASE OF WATER-SOLUBLE SUBSTANCES

This application is a continuation of United States application Ser. No. 07/810,403 filed as PCT/EP91/00307, Feb. 18, 1991, now abandoned.

The present invention relates to microparticles of the microsphere type consisting of a matrix of biocompatible and biodegradable polymer within which a water-soluble substance, in particular a polypeptide is dispersed, the polymer controlling the kinetics of release of the said substance, such that the said substance is progressively released over a defined period of time when the microparticles are placed in an aqueous medium, in particular of the physiological type.

The present invention furthermore relates to a process for preparing the said microparticles.

Such microspheres were initially developed for contraception using steroid hormones (see in particular U.S. Pat. No. 3,773,919).

A difficulty with inventions in this area is the need to determine the polymers exhibiting defined properties as a function of the type of active ingredient to be incorporated, taking into account, on the one hand, its structure and its chemical properties and, on the other hand, the desired kinetics of release. It is also necessary to determine, for a given type of substance, the rate of release and the level of charge ensuring an optimum therapeutic protection for a chosen period when the said substance is a medicinal product.

Furthermore, certain limitations may occur in the preparation process in the technique for incorporating the medicinal product into the polymer which depends on the polymer/medicinal product pair, in particular on the optional existence of a common solvent for the components, the existence of thermal properties of the latter, their miscibility and the like. Moreover, this incorporation must not affect the properties of the active ingredient.

Originally, the aim of the present invention was the preparation of microspheres which would contain a water-soluble polypeptide and in particular calcitonin, and would release the latter in a progressive and continuous manner for a period of at least 8 days and even 30 days for calcitonin once it is injected in man.

The incorporation of active ingredients inside polymer biomaterials in the form of microspheres is performed by the so-called microencapsulation techniques. Microencapsulation includes all the techniques enabling the preparation of individualised particles of the microsphere type whose size ranges from 1 to 250 μm.

Microencapsulation processes are traditionally classified into two groups.

1. So-called microencapsulation by coacervation or by phase separation

First, the product to be encapsulated is dispersed in the solution of a polymer intended to subsequently form the matrix of the microcapsules. Secondly, the coacervation of the polymer is induced by a physico-chemical modification of the reaction medium, in particular by means of a phase separation inducing agent. Thirdly, coacervate droplets that form around the material to be encapsulated are stabilized and solidified by means of a nonsolvent of the polymer, for example heptane.

The main disadvantage of this method is the use of large amounts of solvents with, in addition to cost constraints, problems of toxicity linked to the solvents, such as heptane, used. This is because the techniques by coacervation using heptane do not enable its complete removal. A large amount of residual solvents, of the order of 5 to 10% of heptane, is observed in the microspheres.

Independently of the above, it has also been observed that aggregates of microspheres causing a high loss of yield in the production of these microspheres by this method and sometimes requiring the total rejection of some batches which have thus become unusable, were often produced. The tendency of the microspheres to aggregate causes additional difficulties at the time of suspending the microspheres for injection, in the case of injectable microspheres.

Another disadvantage of the technique by phase separation is the nonhomogeneous distribution of the active substance in the microspheres with irregular release, and in general a first phase of accelerated release ("burst effect"). This is observed in particular when the active substance is suspended in the polymer solution, in particular because it is not soluble in the solvent for the polymer. This generally applies, for example, to polypeptides.

2. Microencapsulation by solvent evaporation

The so-called process by solvent evaporation-(or alternatively by emulsion/evaporation) also leads to the production of microspheres. The active ingredient to be encapsulated is traditionally dispersed in a solution of polymer in a volatile organic solvent. This phase is emulsified by means of a surface-active agent in a non-miscible dispersing medium (water or mineral oil). The organic solvent evaporates with stirring. After the evaporation, the microspheres are recovered by filtration or centrifugation.

The advantages of the technique by emulsion/evaporation are the absence of toxic solvents such as heptane, and the absence of agglomeration of the microspheres.

This technique by emulsion/evaporation is a technique which is simpler, more flexible and easier to industrialize than the technique by phase separation or coacervation. It makes it possible to use reduced amounts of solvent.

It offers a great freedom of action on the various parameters such as the size of the microspheres, the rate of release and the level of charge of the active substance.

Traditionally, this technique is primarily applied to the encapsulation of lipophilic substances such as steroids and nitrosoureas. The microencapsulation of hydrophilic active ingredients requires the use of an apolar dispersing phase such as a mineral oil. Acetone/paraffin systems are conventionally used. However, the levels of incorporation of the hydrophilic active ingredient into the microspheres relative to the amounts employed in the process are fairly low and, moreover, this system involves a limitation with respect to the types of polymers which may be used given that it requires the polymer to be soluble in acetone, which is the case with lactic acid polymers, but which is not the case for lactic acid and glycolic acid copolymers.

This technique by emulsion/evaporation is therefore traditionally recognised as unsuitable for water-soluble peptides and for all water-soluble substances.

The method by phase separation or coacervation is therefore the method selected as being the most adapted to water-soluble substances, in particular to water-soluble polypeptides.

In order to try to obviate the disadvantages of the method by emulsion/evaporation, a method by double emulsion (water/oil/water) has been described in European Patent Application EP 190,833. It is, however, complicated, relatively difficult to industrialize and does not make it possible to obtain the desired kinetics of release according to the present invention.

The object of the present invention is to provide microparticles of the microsphere type for the progressive release of a water-soluble active substance such as a medicinal product, in particular a water-soluble polypeptide, dispersed in a biocompatible and biodegradable polymer matrix enabling a release of the active substance in particular over a period of at least 8 days, and this in a regular manner with in particular the absence of a first phase of accelerated release ("burst effect").

More particularly, another object of the present invention is to enable the progressive release of calcitonin over a period of about 30 days in the same conditions as mentioned above.

Another object is to provide a process for preparing these microspheres, economically and industrially acceptable with in particular a sufficiently high level of incorporation of the active substance to be incorporated in microsphere form.

Another object is to provide microspheres and a process of preparation such that the residual level of solvents, in particular toxic solvents is very low.

According to the present invention, a novel process has been discovered which makes it possible to adapt the technique by emulsion/evaporation to water-soluble substances and in particular to water-soluble polypeptides with a level of incorporation of the substance into the microspheres greater than 90% and a very low level of residual solvent.

In the present application, "level of incorporation" is understood as meaning the level of substance which is found in the microspheres at the end of the process relative to the amount of substance initially employed in the process.

Contrary to the methods described in the literature in which the active substance to be incorporated is a peptide which is placed in microparticulate suspension in the polymer solution, according to the invention, the active peptide substance is first solubilized in a suitable solvent whose characteristics are indicated below.

The subject of the present invention is therefore a process for preparing microspheres of a water-soluble substance, in particular of a water-soluble polypeptide and a biocompatible and biodegradable polymer controlling the kinetics of release of the said substance according to which:

a) the polymer is dissolved in a first volatile organic solvent immiscible with water, b) the water-soluble substance is separately dissolved in a second, non-volatile solvent which is miscible with the first solvent, which is also a solvent for the polymer, and which is miscible with water (the said second solvent therefore in fact constitutes a third solvent between water and the first solvent which is both a solvent for the polymer and a solvent for the water-soluble substance), c) the polymer solution obtained in stage a) and the solution of the active substance obtained in stage b) are mixed, d) an organic phase of the polymer and of the active substance is obtained which is then emulsified in an immiscible dispersant medium consisting of an aqueous phase containing an emulsifying agent, e) the two solvents are then removed from the microspheres being formed, with stirring, the first solvent being removed by evaporation, the second solvent as well as part of the first solvent which is miscible therewith passing into the aqueous phase by a mechanism of phase separation, f) after removal of the solvents, the microspheres formed are recovered, optionally after washing in water and sieving.

Furthermore the microspheres are then preferably treated so as to ensure their preservation.

Volatile organic solvent is understood as meaning an easily evaporable solvent, that is to say evaporable with stirring at room temperature and reduced pressure under air suction.

The second solvent is put in a proportion relative to the first solvent such that there is no precipitation of the polymer in the aqueous phase. This is because if the amount of the said second solvent is too high, the emulsion is no longer obtained, the polymer phase and the aqueous phase become miscible and there is precipitation of the polymer in the aqueous phase. The emulsion remains possible with ratios of second solvent to first solvent ranging up to 70/30 by volume. The minimum proportion of the second solvent relative to the first solvent is of course linked to the level of charge which it is desired to obtain in the case of the active substance in the microsphere. The proportion of 5/95 can be given as a minimum value.

There may be mentioned with no limitation being implied, by way of first solvent, chloroform or dichloromethane and, by way of second solvent, dimethylacetamide DMA, tetrahydrofuran THF, dioxane, DMSO (dimethylsulfoxide) or DMF (dimethylformamide).

In a preferred embodiment of the process according to the invention, the polymer is dissolved in dichloromethane and the water-soluble substance is dissolved in dimethylacetamide (DMA).

The use of the third solvent, which is both a solvent for the water-soluble substance and is miscible with the solvent for the polymer, ensures a homogeneous distribution of the active substance in the polymer phase. However, the advantage of using the third solvent is not, as seen, limited to the mere solubilization of the active substance. Given its miscibility with the aqueous phase, it also contributes to the incorporation process of the active substance into the microsphere.

Thus, contrary to the conventional method by emulsion/ evaporation where the hardening of the microsphere is carried out solely by simple and slow evaporation of the polymer solvent such as $CH_2Cl_2$, in the method according to the present invention, the phenomenon is linked simultaneously to the evaporation of the said first solvent such as $CH_2Cl_2$ and to a rapid phase separation of the second solvent such as DMA towards the aqueous phase. Through the miscibility of the two solvents, some of the first solvent also accompanies the second towards the aqueous phase which considerably reinforces and accelerates its extraction. The method thus combines the processes of evaporation and phase separation by substantially modifying the kinetics of extraction of the solvents as compared with a traditional method of emulsion/evaporation. The kinetics of the incorporation process is therefore modified, which contributes, with the homogeneity of the distribution, to the high level of incorporation observed, as will be described later.

One of the advantages of the process according the invention is to provide microspheres whose residual content of toxic solvent, such as dichloromethane, is very low (in particular lower than 1.5%).

In an improved embodiment of the process according to the invention particularly useful when the said first solvent for the polymer is a toxic solvent, the level of residual solvent may be reduced if the aqueous dispersant phase comprises a third nontoxic solvent miscible with water and miscible with the said first solvent for the polymer. This third solvent is added to the aqueous dispersant phase of the emulsion before the onset of the formation of this emulsion. This addition of such a third solvent makes it possible to promote the removal of the first solvent for the polymer by a better extraction of the latter towards the aqueous phase with which it is otherwise immiscible. The residual level the solvent for the polymer in the microspheres is thus thereby reduced.

The said third solvent is added to the aqueous phase in proportions which continue to make possible the emulsion and the dissolution of the emulsifying agent in this same aqueous phase.

When the solvent for the polymer is dichloromethane, ethanol is advantageously used as said third solvent in a proportion ranging up to 20% by volume of the aqueous phase. The residual level of dichloromethane in the microspheres is thereby considerably reduced, for example to 0.2% relative to the dry weight of the microspheres.

In a specific embodiment of the invention, the water-soluble substance is a polypeptide or one of its pharmaceutically acceptable salts and the polymer is a polymer resulting from the condensation of monomers chosen from alpha-hydroxycarboxylic acids and lactones. Preferably, the polymer is a lactic acid (alpha-hydroxypropionic acid) and glycolic acid (alpha-hydroxyacetic acid) copolymer hereafter abbreviated PLGA, in variable proportions between the lactic acid and glycolic acid units, or a mixture of such polymers.

These polymers are well known in the state of the art. They are known to generate products naturally present and metabolized in the organism and are therefore considered as biodegradable and free from substantial toxicity in the normal conditions of use. They are, moreover, soluble in dichloromethane.

DMA exhibits all the required characteristics as second solvent given that the polymers mentioned above and, in particular the lactic acid and glycolic acid copolymers are soluble therein. DMA is not easily evaporable contrary to dichloromethane. On the other hand, it may be extracted by the aqueous phase with which it is miscible, optionally during the evaporation of the dichloromethane.

In a specific embodiment of the invention, a lactic acid and glycolic acid copolymer (PLGA) which preferably comprises a proportion between the lactic acid and glycolic acid units ranging from 40:60 to 75:25 respectively, is used.

The molecular mass of the polymer will preferably be between 20,000 and 100,000. The water-soluble polypeptides according to the invention have a molecular mass normally between 200 and 100,000.

Thus, the process according to the invention is applicable to the most diverse polypeptides such as hormones, cytokines, growth factors, neuropeptides, coagulation factors, enzymes, anti-enzymes, soluble receptors or biologically active derivatives of these substances. There may also be mentioned, in particular, with no limitation being implied, human growth hormone (HGH), bovine growth hormone (BGH), porcine growth hormone (PGH), ovine growth hormone and the like) somatomedins, IGF-1, IGF-2 and insulins; LH-RH and its analogues, GH-RP and its analogues; somatostatin and its analogues; ACTH, ADH, PTH, PTH 1-34, CRH, GH-RH, inhibit, activin, motilin, relaxin, ANF, endothelins, their derivatives and analogues; IL1, IL2, IL3, IL4, IL5, IL6, IL7, IL8, IL9, G-CSF, GM-CSF, M-CSF, alpha, beta and gamma interferons, alpha and beta TNF, alpha and beta TGF, PDGF, EGF, FGF, osteogenins, their analogues and derivatives; TPA, factor VIII, von Willebrandt factor, hirudin, echistatin, bitisatin, alpha-1-antitrypsin, superoxide dismutase, soluble CD4 and their analogues and derivatives; peptide derivatives or analogues of adhesion molecules, of lymphocyte receptors or of components of the major histocompatibility complex; and calcitonins whether they are obtained from man, pig, salmon, eel or from another species, as well as their analogues and derivatives.

According to the process of the invention, the level of charge of substance in the polymer may rise from 0.01 to 40%. Level of charge is understood as meaning the ratio by weight of the substance to the weight of the polymer in the microsphere. Generally, this level of charge will preferably be from 1 to 10% depending on the desired therapeutic protection.

Thus, in the case of calcitonin, its solubility in DMA which is 50mg/ml makes it possible to envisage a level of charge ranging up to 31.5% of salmon calcitonin in 50:50 PLGA microspheres taking into account the maximum DMA/$CH_2Cl_2$ proportion of 70/30 which may be used. However, the best therapeutic protection is obtained with a level of charge of only 1 to 2% in the case of salmon calcitonin, and 10% in the case of human calcitonin which is less active. It is therefore clear that the process according to the invention produces no practical limitation with respect to the level of charge of the substance in the microsphere.

Water-soluble polypeptide is understood, in the present application, as meaning a solubility of not less than 0.1 mg/ml in water.

When the solubility of the polypeptide is too low for the level of charge which it is desired to obtain in the microsphere taking into account the target therapeutic protection, a mixture of DMA and water may be used as second solvent, it being possible for the amount of water in proportion by volume relative to the DMA to rise up to 50%.

According to the invention, a ballasting substance may be added into the polymer phase at the same time as the active substance in order to facilitate the release by accelerating and regulating the kinetics of release. This ballast may be either dissolved or suspended in the polymer phase. The most diverse ballasts may be used such as proteins like HSA, gelatin, sugars, polysaccharides, amino acids or polypeptides. The level of charge of ballast may reach 5%.

In the process according to the invention, preferably, the emulsification is carried out with vigorous stirring so as to obtain microparticles less than 200μ in size, preferably between 25 and 200μ. Thus, injectable microspheres are obtained when they are formulated into an injectable solute.

This is because the size of the microspheres depends on the force of the stirring and in particular the speed imposed on the helix during the emulsion (if it increases, the size decreases). It also depends on the concentration of emulsifier in the aqueous phase (if it increases, the size decreases), and finally, of course, on the size of the sieve mesh. A maximum distribution of the mean size of the microspheres between 25μ and 200μ is easily and reproducibly obtained by acting on the aforementioned parameters.

Gelatin, carboxymethylcellulose, methylcellulose, hydroxypropyl cellulose, hydroxyethyl cellulose, polyvinyl alcohol (PVA) or alternatively nonionic detergents such as Tween 80 or ionic detergents may be mentioned by way of emulsifying agent present in the aqueous phase, with no limitation being implied.

The concentration of the emulsifier in the aqueous phase influences the size of the microspheres. The latter increases as the concentration of emulsifier decreases. According to the invention, the concentration of emulsifier in the aqueous phase may range from 0.1 to 10% (weight/volume).

In a specific embodiment, gelatin, which is particularly well accepted as a product which can be injected into the organism has been used as emulsifying agent.

The process according to the invention offers the usual advantages of an emulsion/evaporation technique as compared with the phase separation or coacervation technique:

- absence of toxic solvent other than the solvent for the polymer,
- absence of agglomeration of microspheres (easier industrialization and injection),
- absence of handling of a large amount of solvent during the industrial production,
- possibility of acting on various parameters in order to easily modulate the kinetics of release as a function of the therapeutic application concerned: the characteristics of the polymer, the presence of ballast, the size of the microspheres, the level of charge of water-soluble substance.

The other advantages specific to the use of a third solvent for solubilizing the water-soluble substance are:

- a level of incorporation of the substance which may be higher than 90%,
- the regular and homogeneous distribution of the water-soluble substance solubilized in the polymer, and in the final microsphere,
- the possibility of achieving substantial levels of charge of water-soluble substance while preserving a high level of incorporation,
- a reduction of the residual level of the solvent for the polymer in the final product,
- the absence or the reduction of "burst" effect during the kinetics of release of the substance.

The subject of the present invention therefore is also microparticles of the microsphere type for the progressive release of a water-soluble active substance such as a medicinal product, in particular of a water-soluble polypeptide regularly distributed within a matrix of a biocompatible and biodegradable polymer which is soluble in an organic solvent which is immiscible water, enabling a release of the said active substance over a period of at least 8 days, and this in a regular manner with in particular the absence of a first phase of accelerated release.

According to the invention, the microspheres exhibit a residual level of solvent lower than 1.5%, preferably lower than 0.5% (w/w) and in particular are free from heptane. In effect, the level of DMA is lower than 0.5%, and in general even of the order of 0.1% (w/w) and the level of $CH_2Cl_2$ is generally lower than 0.5%, and even often lower than 0.2% (w/w). Consequently, one of the characteristics of the microspheres according to the present invention is to have a level of residual toxic solvent lower than 0.5%, preferably lower than 0.2% by weight relative to the dry weight of the microspheres.

The polymer will advantageously be a dichloro-methane-soluble polymer, in particular a lactic acid and glycolic acid copolymer.

The microspheres obtained according to the invention are moreover characterized by the homogeneous distribution of the active substance which manifests itself by the high reduction of the burst effect, by a low tendency to agglomerate which distinguishes them from the microspheres obtained by coacervation which is usually described for the encapsulation of peptides, and by substantially reduced residual levels of solvents.

Other characteristics and advantages of the present invention will emerge from the following examples:

EXAMPLE 1

Preparation of Calcitonin Microsphere in a Matrix of Lactic Acid and Glycolic Acid Copolymer 5 g of 50/50 PLGA (lactic acid and glycolic acid copolymer: 50/50) are dissolved in 40 g of dichloromethane $CH_2Cl_2$.

5 mg of salmon calcitonin are dissolved in 5 ml of dimethylacetamide (DMA). The solubilized peptide is mixed with the polymer phase. 150 ml of 10 mM phosphate buffer at pH 8 containing 4% (weight/volume) of gelatin are added to this mixture.

An emulsion is produced by mixing the polymer/calcitonin phase with the aqueous phase containing the gelatin by means of a helix revolving at 1,500 revolutions/minute for 1 minute.

The evaporation of the solvent for the polymer $CH_2Cl_2$ is carried out by maintaining a stirring of 500 revolutions/minute in the emulsified mixture. The extraction of the DMA towards the aqueous phase is performed in parallel. This evaporation is carried out at room temperature with air suction until complete evaporation of the solvent.

The emulsified mixture is then diluted two-fold with water and stirred 1 hour at 37° C.

The microspheres thus obtained are then sieved in water in order to select those having a suitable size in order to be injected, that is to say between 25 and 200μ.

The sieved microspheres are then dried under vacuum at room temperature.

After drying, the microspheres are fully individualized and are easily resuspended in a physiological medium for injection. Microscopic examination confirms the homogeneity and the complete absence of agglomeration of the microspheres.

The levels of residual solvents in the microspheres are:

solvent for the polymer CH2Cl$_2$: lower than 0.5% relative to the dry weight of the microspheres, third solvent DMA: lower than 0.1% relative to the dry-weight of the microspheres

EXAMPLE 2

Modification of the Extraction of the Solvent for the Polymer by Using the Third Solvent This example illustrates an improvement of the removal of the first solvent ($CH_2Cl_2$) by the mechanism of phase separation by virtue of the presence of the second solvent (DMA).

Materials

Polymer phase:

50/50 PLGA η= 0.8: 2.5 g salmon CT : 5 mg level of charge of 0.2%/PLGA.

| A | B |
|---|---|
| $CH_2Cl_2$ volume/DMA volume = 9/1 | $CH_2Cl_2$ volume/DMA volume = 7/3 |
| $CH_2Cl_2$ = 20.25 g | $CH_2Cl_2$ = 15.75 g |
| DMA = 2.25 ml | DMA = 6.75 ml |

Aqueous phase:

10 mM phosphate buffer, pH 8 with 4% gelatin as emulsifier: 75 ml.

Method

The peptide is solubilized in the volume of DMA used in the reaction.

This solution is then added to the PLGA solubilized in $CH_2Cl_2$.

The aqueous phase is mixed with this PLGA phase by means of a helix revolving at 1,500 r/min for 1 minute.

A stirring of 500 r/min is maintained for 12 hours at room temperature with air suction at the surface of the reaction medium.

The microspheres are then sieved and washed in water.

They are then dried in an oven at room temperature under vacuum.

Results

The residual level of $CH_2Cl_2$ in these microspheres is measured by gas chromatography.

|  | A | B |
|---|---|---|
| $CH_2Cl_2$ volume/DMA volume | 9/1 | 7/3 |
| Residual level of $CH_2Cl_2$ (%) ($CH_2Cl_2$ weight/microsphere weight) | 2.58% | 0.44% |

EXAMPLE 3

Level of Incorporation of Calcitonin and "Burst" Effect

The microspheres obtained by the process according to the invention are characterized by a reduction of the "burst effect" and a highly improved level of incorporation compared to the conventional process by emulsion/evaporation.

The table below presents the results for the preparations obtained with the conventional method by emulsion/evaporation compared to the method according to the invention for various polymers.

The presence of a "burst" effect essentially reflects nonhomogeneity of the distribution of the active ingredient in the PLGA matrix.

In the "conventional" method by emulsion/evaporation followed and the method according to the invention, 2.5 g of polymer dissolved in 20 g of $CH_2Cl_2$ are used. 5 mg of salmon calcitonin are used and 10 mg of gelatin as ballast.

In the "conventional" method, the calcitonin and the ballast are suspended in the polymer phase. In the method according to the invention, the calcitonin is dissolved in 2.5 ml of DMA to which the ballast is added in the form of a 5% aqueous solution of gelatin (0.2 ml). This calcitonin-ballast-DMA mixture is then added to the polymer phase so as to form a single homogeneous phase.

In the methods, the aqueous phase consists of 75 ml of 4% gelatin in water (weight/volume). The two phases are emulsified by stirring with a helix at 1,500 revolutions/minute for i minute. A stirring of 500 revolutions/minute is maintained, on the one hand, in order to facilitate the evaporation of the $CH_2Cl_2$ and, on the other hand, in the method according to the invention, to enable the DMA to be extracted in the aqueous phase, in both cases, the microspheres are washed in water and collected on sieves.

|  | "Conventional" method by emulsion/ evaporation | Emulsion/ evaporation method according to the invention |
|---|---|---|
| Distribution of the peptide in the PLGA phase: | By suspension | By dissolution by means of a third solvent (DMA) |
| Level of incorporation of calcitonin in the PLGA microspheres | | |
| Example 3-1: 50/50 PLGA of Mw (sic) = 50,000 n = 0.5 | 29.8% | 79.4% |
| Example 3-2: 50/50 PLGA of Mw (sic) = 91,000 n = 0.7 | 39.7% | 83.8% |
| Example 3-3: 50/50 PLGA of Mw (sic) = 115,000 n= 0.8 | 52.6% | 92.4% |
| "Burst" effect observed after the first day of release in vitro | | |
| Example 3-1: | 12% | 5% |
| Example 3-2: | 30% | 3% |
| Example 3-3: | 11% | 5% |

The viscosity of the polymer is represented by the letter n. It is linked to the molecular mass Mw (sic) by the Kuhn-Mark-Houwink relationship: $n=K M^{-a}$ where K and a are constants for a polymer-solvent system at a fixed temperature.

EXAMPLE 4

Kinetics of Release—Principal Adjustable Parameters

1) Choice of the polymer

The polymer of composition 50/50 is more rapidly degraded than the copolymers having other proportions of lactic acid and glycolic acid. (See reference: Miller R. A., Brady J. M. and Cutright D. E.—J. Biomed. Mater. res. (sic), 11, 711, 1977).

The intrinsic viscosity of the PLGA which is moreover mainly dependent on the size of the polymers is also involved in the kinetics of release. Thus, for calcitonin microspheres prepared with 50/50 PLGAs of differing viscosities., a release in vitro of calcitonin shows that the higher the intrinsic viscosity of the PLGA (the higher the molecular mass of PLGA) the slower is-the release of calcitonin into the external medium. Thus, for an incorporation of 50/50 PLGA of viscosity equal to 0.4 (MW measured by GPC: 36,000), 0.5 (50,000) or 0.7 (91,000), the percentage of calcitonin released in vitro after 14 days is 79.5, 75.5 or 43.2% respectively.

2) Size of the microspheres

Example 4a: Influence of the size of the microspheres on the release of the active ingredient Calcitonin microspheres were prepared according to the following procedure.

Materials

Polymer phase:

| Polymer phase: | |
|---|---|
| 50/50 PLGA polymer n = 0.8 | 2.5 g |
| solvent for the PLGA: $CH_2Cl_2$ | 20.0 g |
| peptide: CTs (salmon calcitonin) | 10.0 mg |
| level of charge of 0.4%/PLGA | |
| $^{125}$I-labelled peptide: $^{125}$I-CTs | 2.39 $10^6$ cpm |
| ballast: lactose | 5.0 mg |
| level of charge of 0.2%/PLGA | |
| "third solvent": DMA | 2.5 ml |
| Aqueous phase: | |
| 10 mM phosphate buffer, pH 8 with 4% of gelatin (= emulsifier) | 75.0 ml |

Method:

The peptide, the tracer and the ballast are solubilized in DMA.

They are then added to the polymer in solution in $CH_2Cl_2$ in order to form a homogeneous phase, the polymer phase.

Emulsion: the aqueous phase is then superposed on the polymer phase and mixed with the polymer phase by means of a helix revolving at 1,500 revolutions/min for one minute.

Evaporation: a stirring of 500 revolutions/min is maintained for ±12 hours, at room temperature, with suction of air at the surface of the emulsified mixture.

The emulsion is then diluted 2-fold in water-and stirred for 1 hour, at 37° C.

The microspheres are recovered in water on successive sieves of progressively smaller meshes, 200-100-50-20 microns.

They are then dried for 24 hours in an oven under vacuum, at room temperature.

They are then irradiated at 2.5 Mega Rad.

Results:

Size of the microspheres obtained:

| Size (x) in microns | 25<x<50μ | 50<x<100μ | 100<x<200μ | x>200μ |
|---|---|---|---|---|
| Percentage by weight of the microspheres | 7.5% | 39.3% | 46.2% | 0.7% |

The level of incorporation of calcitonin into the microspheres: it is measured by means of the tracer ($^{125}$I-CTs) introduced in the preparation and by taking into account the yield by weight of the microspheres relative to the weight of the polymer employed. A total of 85.1% of CTs incorporated is found.

Release "in vitro" of calcitonin: 200 mg of microspheres are placed in 10 ml of 10 mM phosphate buffer, pH 7 containing 0.5% of BSA at 37° C. in an oscillating bath.

| Size of the microspheres | 25–50μ | 50–100μ | 100–200μ |
|---|---|---|---|
| After: 1 day | 11.2% | 3.2% | 2.8% |
| 3 days | 16.0% | 4.5% | 4.0% |
| 4 days | 16.5% | 5.0% | 4.7% |
| 7 days | 19.8% | 5.5% | 4.9% |
| 10 days | 25.2% | 7.4% | 6.4% |
| 14 days | 31.4% | 7.7% | 7.0% |
| 25 days | 73.0% | 31.6% | 31.0% |
| 28 days | 100.0% | 40.2% | 39.0% |
| 35 days | — | 64.5% | 56.0% |
| 40 days | | 89.0% | 79.0% |
| 42 days | | 100.0% | 89.0% |
| 45 days | | — | 100.0% |

Example 4b: Parameters influencing the size of microspheres

Example 4b-I: rate of emulsion

50/50 PLGA: 2.5 g dissolved in $CH_2Cl_2$:20 g Salmon calcitonin: 5 mg dissolved in 2.5 ml of DMA and then added to the polymer phase.

Aqueous phase: 75 ml of 5% gelatin (weight/volume) in water.

The 2 phases are emulsified
either by stirring with a helix at 2,000 revolutions/ minute for 1 minute,
or by stirring with a helix at 500 revolutions/ minute for 1 minute.

Evaporation of the $CH_2Cl_2$ and the passage of DMA in water are carried out with continuous stirring of 500 revolutions/minute.

After several washes in water, a sample of microspheres is analyzed in the "Fritsch particle sizer" (Analysette 22).

Results

| Percentage of the microspheres (by weight) having a size less than | Emulsion at 2,000 r/min Size of the microspheres (μ) | Emulsion at 500 r/min Size of the microspheres (μ) |
|---|---|---|
| 10% < | 16.4 | 78.9 |
| 30% < | 35.2 | 164.0 |
| 50% < | 52.3 | 212.0 |
| 70% < | 73.0 | 271.0 |
| 90% < | 126.0 | 351.0 |

Example 4b-II: The concentration of the emulsifier

50/50 PLGA: 2.5 g dissolved in $CH_2Cl_2$: 20 g Salmon calcitonin: 5 mg dissolved in 2.5 ml of DMA and then added to the polymer phase.

Aqueous phase:
either: 75 ml of 5% gelatin (weight/volume) in water, or: 75 ml of 1% gelatin (weight/volume) in water.

The two phases are emulsified by stirring with a helix at 2,000 revolutions/minute for 1 minute.

The evaporation of $CH_2Cl_2$ and the passage of the DMA in water are carried out with a stirring of 500 revolutions/minute with a helix.

After several washes in water, the microspheres are analyzed in the "Fritsch Particle Sizer" (Analysette 22).

Results

| Percentage of the microspheres (by weight) having a size lower than | Emulsifier: 5% gelatin Size of the microspheres (μ) | Emulsifier: 1% gelatin Size of the microspheres (μ) |
| --- | --- | --- |
| 10% < | 16.4 | 37.4 |
| 30% < | 35.2 | 73.6 |
| 50% < | 52.3 | 104.0 |
| 70% < | 73.0 | 140.0 |
| 90% < | 126.0 | 215.0 |

3) Choice of the ballast

The presence or the concentration of ballast in microspheres as well as the nature of the ballast-may influence the kinetics of release of calcitonin as shown by the following experiment:

Materials:

Polymer phase:

50/50 PLGA: 2.5 g dissolved in $CH_2Cl_2$: 20.0 g salmon calcitonin: 10 mg dissolved in: DMA: 2.5 ml ballast:

| A | B | C |
| --- | --- | --- |
| Without | Lactose 0.2% | Gelatin 0.2% |

Aqueous phase:

10 mM phosphate buffer, pH 8 75 ml with 4% of gelatin (weight/volume)

Method:

The two phases are emulsified by stirring with a helix at 1,500 revolutions/minute for one minute.

A stirring of 500 revolutions/minute is then maintained until complete evaporation of the $CH_2Cl_2$ and passage of the DMA in the aqueous phase.

After several washes with water, the microspheres are recovered on sieves and dried under vacuum.

Results:

Release "in vitro" obtained in the same conditions as in point 2) of Example 3.

| | | Cumulative percentage of CTs released | |
| --- | --- | --- | --- |
| | A without ballast | B (+0.2% lactose) | C (+0.2% gelatin) |
| After: 1 day | 2.0% | 2.8 | 6 |
| 2 days | 2.2% | 4.0 | 8 |
| 7 days | 3.4% | 5.0 | 11 |
| 12 days | 4.3% | 7.4 | 15 |
| 20 days | 16.0% | 22.0 | 36 |
| 25 days | 25.0% | 31.0 | 46 |
| 30 days | 32.0% | 41.0 | 59 |
| 35 days | 39.0% | 56.0 | 83 |
| 37 days | 44.0% | 66.0 | 88 |
| 40 days | 59.0% | 79.0 | 100 |
| 42 days | 69.0 | 100.0 | — |
| 48 days | 100.0 | — | — |

4) Level of charge of peptide

Materials

Polymer phase:

50/50 PLGA: 0.5 g dissolved in: $CH_2Cl_2$: 10 g

DMA= 3 ml in which is dissolved salmon calcitonin in the following amount:

| A | B |
| --- | --- |
| 10 mg Level of charge of 2% | 25 mg Level of charge of 5% |

Ballast: without Aqueous phase:

10 mM phosphate buffer, pH 8 with 4% gelatin (weight/volume): 75 ml.

Method

Release "in vitro" obtained in the same conditions as in point 2) of Example 3.

| | Cumulative percentage of CTs released | |
| --- | --- | --- |
| Level of charge of salmon calcitonin | A 2% | B 5% |
| After: 1 day | 3.0% | 6.5% |
| 4 days | 4.8% | 13.0% |
| 6 days | 5.7% | 16.0% |
| 10 days | 7.4% | 18.5% |
| 15 days | 8.6% | 23.0% |
| 21 days | 9.7% | 27.0% |

EXAMPLE 5

Reduction of the Residual Level of Toxic Solvent in the Microspheres

Materials

50/50 PLGA: 1 g dissolved in 7 g of $CH_2Cl_2$.

Salmon calcitonin: 20 mg dissolved in 2 ml of DMA and then added to the polymer phase.

Aqueous phase:
 a.*either: 100 ml of 5% gelatin (weight/volume) in 10 mM phosphate buffer, pH 8 (sic).
 b.*or: a mixture of 80 ml of 5% gelatin (weight/volume) in 10 mM phosphate buffer, pH 8 (sic)+ 20 ml of ethanol.

Method

The two phases are emulsified by means of a helix revolving at 1,500 revolutions/minute, for 1 minute.

A stirring of 500 revolutions/minute for 12 hours at 37° C. with suction of air enables the evaporation of $CH_2Cl_2$ and the passage of DMA towards the aqueous phase.

The microspheres are recovered on successive sieves of 200 and 25 microns.

They are then dried for 24 hours in an oven under vacuum at room temperature and then irradiated at 2.5M Rad.

Results

The levels of residual dichloromethane in the dry microspheres (fraction of 25 to 200 microns) are determined by aqueous phase chromatography. These levels are expressed as percentage of solvent relative to the dry weight of the microspheres.

| Method of preparation | Residual level of CH$_2$Cl$_2$ |
| --- | --- |
| a. without ethanol in the aqueous phase | 1.36% |
| b. with 20% of ethanol in the aqueous phase | 0.14% |

EXAMPLE 6

Adaptation of the Technique to Other Polypeptides

The application of the technique is conditioned by the solubility of the polypeptides in the third solvent. This property is common to numerous polypeptides, as has been shown for calcitonin.

Example:
 LHRH ("Luteininizing Hormone Releasing Hormone") is soluble at not less than 50 mg/ml in DMA.
 HGH ("Human Growth Hormone") is soluble at 2.6 mg/ml of DMA.

In order to increase the solubility of certain polypeptides which are less soluble in the "third solvent", it is possible to add an aqueous solution of the peptide to the "third solvent" which is of course miscible with water.

Accordingly, it has been possible to incorporate the following peptides in the PLGA microspheres by the technique according to the invention: calcitonin, hGh (sic), bGH (sic), ANF, somatostatin, LHRH, insulin, somatomedin C, ACTH, ADH, TPA as well as various cytokines: erythropoietin, GMCSF, GCSF, IL3, IL1, IL6, IL2, IL4, TNF, alpha interferon, beta interferon, beta TGF, PDGF and EGF.

The table below collates the levels of incorporation obtained for the various peptides using the "standard" procedure described below according to the invention without individual optimization for each peptide. The values therefore represent a minimum level of incorporation. The standard procedure used is as follows:

Materials
 50/50 PLGA: 2.5 g dissolved in 20 g of CH$_2$Cl$_2$. Third solvent: DMA: 2.5 ml in which the active ingredient is dissolved.
Aqueous phase:
75 ml of 4% gelatin (weight/volume) in 10 mM phosphate buffer, pH 8.
Method
 The polymer phase in which the active ingredient is dissolved by means of the third solvent, is emulsified with the aqueous phase by a helix stirred at 1,500 revolutions/minute and this for one minute.

A stirring of 500 revolutions/minute is maintained at room temperature with suction of air in order to facilitate the evaporation of CH$_2$Cl$_2$ and the passage of the third solvent in the water.

The microspheres are then recovered on a sieve after having been abundantly washed in water.

They are then dried at room temperature under vacuum.

| Active ingredient incorporated in the microspheres | Percentage of the peptide incorporated |
| --- | --- |
| hGH (sic) (human growth hormone) | 77.0% |
| Somatomedin C (IGF-1) | 52.0% |
| TPA (Tissue Plasminogen Activator) | 96.0% |
| Insulin | 98.0% |
| IL4 | 77.5% |
| IL6 | 43.8% |
| Erythropoietin | 40.0% |
| TNF | 66.4% |
| Salmon calcitonin | 92.4% |
| Human calcitonin | 85.0% |
| IL2 | 78.5% |
| GRH | 84.0% |
| LHRH | 75.0% |
| GMCSF | 59.0% |
| PTH (1–34) | 54.0% |
| Somatostatin | 82.0% |
| ANP (or ANF) | 72.0% |
| Alpha interferon | 77.0% |

We claim:

1. A process for preparing microparticles of the microsphere type of a water-soluble polypeptide or a pharmaceutically acceptable salt thereof and a biocompatible and biodegradable polymer, comprising the steps of:

a) dissolving a biocompatible and biodegradable polymer in a first volatile organic solvent immiscible with water, b) separately dissolving water-soluble polypeptide in a second solvent which is nonvolatile, miscible with said first solvent, a solvent for said polymer, and miscible with water, c) mixing the solution of said polypeptide and the solution of said polymer to produce an organic phase containing said polymer and said polypeptide, d) emulsifying said organic phase in an immiscible dispersant aqueous phase containing an emulsifying agent, e) removing the two solvents from the microspheres being formed, with stirring, the first solvent being removed by evaporation, the second solvent as well as part of the first solvent which is miscible therewith being removed by passage towards the aqueous phase by a mechanism of phase separation, and f) after removal of the solvents, recovering the microspheres formed, optionally after washing in water and sieving.

2. Process according to claim 1, wherein said aqueous dispersant phase comprises a third solvent which is miscible with water and miscible with said first solvant.

3. Process according to claim 1, wherein said first solvant is dichloromethane and said second solvent is dimethylacetamide.

4. Process according to claim 2, wherein said third solvent is ethanol.

5. Process according to claim 1, wherein said polymer is a lactic acid and glycolic acid copolymer.

6. Process according to claim 1, wherein said polymer is a lactic acid and glycolic acid copolymer which comprises a proportion between the lactic acid and glycolic acid units of 40:60 to 75:25 respectively.

7. Process according to claim 1, wherein said concentration of emulsifying agent in the aqueous phase is between 0.1 and 10% (weight/volume).

8. Process according to claim 1, wherein the second nonvolatile solvent is selected from the group consisting of dimethylacetamide, tetrahydrofuran, dioxane, dimethyl sulfoxide and dimethylformamide.

9. The process of claim 1, wherein in at least one of steps (b) or (c), a ballast is added which is dissolved or suspended in the organic polymer phase resulting from step (c).

* * * * *